(12) United States Patent
Tobin et al.

(10) Patent No.: US 6,277,586 B1
(45) Date of Patent: Aug. 21, 2001

(54) CLONED GLUTAMIC ACID DECARBOXYLASE

(75) Inventors: Allan J. Tobin, Los Angeles; Mark G. Erlander, Tarzana; Daniel L. Kaufman, Santa Monica, all of CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 09/372,752

(22) Filed: Aug. 11, 1999

Related U.S. Application Data

(62) Division of application No. 07/586,536, filed on Sep. 21, 1990.

(51) Int. Cl.$^7$ .................................................... G01N 33/68
(52) U.S. Cl. ......................... 435/7.6; 435/7.92; 436/543; 436/546
(58) Field of Search .............................. 435/7.1, 7.2, 7.4, 435/7.6, 7.92; 436/543, 544, 545, 546

(56) References Cited

U.S. PATENT DOCUMENTS

| | | | |
|---|---|---|---|
| 5,475,086 | * 12/1995 | Tobin et al. | 530/325 |
| 5,512,447 | * 4/1996 | Baekkeskov et al. | 435/7.4 |
| 5,645,998 | * 7/1997 | Atkinson et al. | 435/7.4 |
| 5,674,978 | * 10/1997 | Tobin et al. | 530/326 |
| 5,705,626 | * 1/1998 | Tobin et al. | 536/23.5 |
| 5,762,937 | * 6/1998 | Atkinson et al. | 424/198.1 |
| 5,792,620 | * 8/1998 | Lernmark et al. | 435/7.95 |
| 5,846,740 | * 12/1998 | Tobin et al. | 435/7.4 |
| 5,998,366 | * 12/1999 | Tobin et al. | 514/12 |
| 6,011,139 | * 1/2000 | Tobin et al. | 530/388.26 |

* cited by examiner

*Primary Examiner*—Robert D. Budens
(74) *Attorney, Agent, or Firm*—Burns, Doane, Swecker & Mathis, LLP

(57) ABSTRACT

The invention provides cDNA molecules comprising a part of the cDNA sequence of $GAD_{65}$ which encode at least one epitope for autoantibodies to $GAD_{65}$. The invention also provides cloning vehicles capable of replication and expression comprising cDNA molecules coding for $GAD_{65}$. The invention further provides for hosts transformed with a vehicle having a cDNA molecule coding for $GAD_{65}$. In another embodiment, the invention provides for the detection of autoantibodies to $GAD_{65}$ using the $GAD_{65}$ polypeptides coded for by the cDNA molecules of the invention.

6 Claims, 12 Drawing Sheets

```
GGGCGTGCGGGGTCGAGCCGAAGCAGCTTGCCCGCAGCCACTCGGAGGGACCAGCCA
                                              10                             30                                50
                                                                                    M   A   S   P   G   S   G   F   W   S   F   G   S   E   D   G
GACTAGCAGAACCCATGGCATCTCCGGGCTCTGGCTTTTGGTCCTTCGGATCTGAAGATG
              70                               90                              110
  S   G   D   P   E   N   P   G   T   A   R   A   W   C   Q   V   A   Q   K   F
GCTCTGGGGATCCTGAGAACCCGGGAACCAGCCTGGTGCCAGTGCCCAAAAGT
            130                              150                             170
  T   G   G   I   G   N   K   L   C   A   L   L   Y   G   D   S   E   K   P   A
TCACGGGCGGCATCGGAAACAAGCTATGCGCTCTGCTCTACGGAGACTCTGAGAAGCCAG
             190                              210                            230
  E   S   G   G   S   V   T   S   R   A   A   T   R   K   V   A   C   T   C   D
CAGAGAGCGGGGAGCGTGACCTCGCGGGCCGCCACTCGGAAGGTCGCCTGCACCTGTG
             250                              270                             290
  Q   K   P   C   S   C   P   K   G   D   V   N   Y   A   L   H   A   T   D
ACCAAAAACCCTGCAGCTGCCCCAAAGGAGATGTCAATTATGCACTTCTCCAGGCAACAG
             310                              330                             350
  L   P   A   C   E   G   E   R   P   T   L   A   F   L   Q   D   V   M   N
ACCTGCTGCCAGCCTGTGAAGGAGAAAGGCCCACTCTCGCATTTCTGCAAGATGTAATGA
            370                              390                             410
  I   L   Q   Y   V   V   K   S   F   D   R   S   T   K   V   I   D   F   H
ACATTTTGCTTCAGTAGCTTCTTCAAGAGTATAATTGGATAGATCAACTAAAGTGATTGATTTCC
            430                              450                             470
  Y   P   N   E   L   L   Q   E   Y   N   W   E   L   A   D   Q   P   Q   N   L
ATTACCCCAATGAGCTTCTTCAAGAGTATAATTGGGAATTGGCAGACCAACCGCAAAATC
            490                              510                             530
  E   E   I   L   T   H   C   Q   T   T   L   K   Y   A   I   K   T   G   H   P
TGGAGGAAATTTTGACGCACTGCCAAACAACTCTAAAATATGCGATTAAAACAGGGCATC
            550                              570                             590
  R   Y   F   N   Q   L   S   T   G   L   D   M   V   G   L   A   A   D   W   L
CCCGATATTTTAATCAGCTGTCTACCGGATTGGATATGGTTGGATTAGCAGCAGATTGGT
            610                              630                             650
  T   S   T   A   N   T   N   M   F   T   Y   E   I   A   P   V   F   V   L   L
TGACATCAACAGCAAAACACGAACATGTTTACCTATGAGATCGCCCCTGTATTTGTACTAC
```

FIG. 2A

```
  E   Y   V   T   L   K   K   M   R   E   I   I   G   W   P   G   G   S   G   D
670                         690                          710
TGGAATATGTGACACTAAAGAAGATGAGGGAAATCATTGGCTGGCCAGGAGGCTCTGGCG
     730                         750                         770
  G   I   F   S   P   G   G   A   I   S   N   M   Y   A   M   L   I   A   R   Y
ATGGAATCTTTTCCTGGTGGTGCCATCTCCAACATGTACGCCATGCTCATTGCCCGCT
     790                         810                         830
  K   M   F   P   E   V   K   E   K   G   M   A   A   V   P   R   L   I   A   F
ATAAGATGTTTCCAGAAGTCAAGGAAAAGGGGATGGCGGCCGTGCCCAGGCTCATCGCAT
     850                         870                         890
  T   S   E   H   S   H   F   S   L   K   K   G   A   A   A   L   G   I   G   T
TCACGTGTCAGAGCATAGTCACTTTTCTCAAGAAGGGAGCTGCAGCCTTGGGGATCGGAA
     910                         930                         950
  D   S   V   I   L   I   K   C   D   E   R   G   K   M   I   P   S   D   L   E
CAGACAGCGTGATTCTGATTAAATGTGATGAGAGGGGAAAATGATCCCCATCTGACCTTG
     970                         990                        1010
  R   R   I   L   E   V   K   Q   K   G   F   V   P   F   L   V   S   A   T   A
AAAGAAGAATCCTTGAAGTCAAACAGAAACAGGATTTGTTCCTTTCGTGGTGAGTGCCACAG
    1030                        1050                        1070
  G   T   T   V   Y   G   A   F   D   P   L   L   A   V   A   D   I   C   K   K
CTGGAACCACTGTGTACGGGGCTTTTGATCCTCTCTTGGCTGTAGCTGACATCTGCAAAA
    1090                        1110                        1130
  Y   K   I   W   M   H   V   D   A   A   W   G   G   G   L   M   S   R   K
AATATAAGATCTGGATGCATGTGGATGCTGCTTGGGGTGGAGGGTTACTGATGTCTCGGA
    1150                        1170                        1190
  H   K   W   K   L   N   G   V   E   R   A   N   S   V   T   W   N   P   H   K
AACACAAGTGGAAGCTGAACGGTGTGGAGAGGGCCAACTCTGTGACATGGAATCCCCACA
    1210                        1230                        1250
  M   M   G   V   P   L   Q   C   S   A   L   L   V   R   E   E   G   L   M   Q
AGATGATGGGTGTCCCCTTGCAATGTTCGGCTCTCCTGGTCAGAGAGAGGGACTGATGC
```

FIG. 2B

```
                                          1290                    1310
     S  C  N  Q  M  H  A  S  Y  L     F  Q  Q  D  K  H  Y  D  L  S
     AGAGCTGCAACCAGATGCATGCTTCCTACCTCTTTCAGCAAGATAAGCACTATGACCTGT
                    1270                   1330                     1370
     Y  D  T  G  D  K  A  L     Q  C  G  R  H  V  D  V  F  K  L  W
     CCTATGACACGGGAGACAAGGCCTTGCAGTGTGGACGCCACGTCGATGTCTTTAAATTAT
                    1390                    1410                    1430
     L  M  W  R  A  K  G  T  G     F  E  A  H  I  D  K  C  L  E
     GGCTCATGTGGAGAGCAAAGGGGACTACTGGATTTGAAGCTCACATTGATAAGTGTTTGG
                    1450                    1470                    1490
     L  A  E  Y  L  Y  N  I  I  K  N  R  E  G  Y  E  M  V  F  D
     AGCTGGCAGAGTATTTATACAATATCATTAAAAACCGAGAAGGATATGAAATGGTGTTCG
                    1510                    1530                    1550
     G  K  P  Q  H  T  N  V  C     F  W  F  V  P  P  S     L  R  V  L
     ATGGGAAGCCTCAGCACACAAATGTCTGCTTCTGGTTTGTACCCTCCTAGTTTGCGAGTTC
                    1570                    1590                    1610
     E  D  N  E  E  R  M  S  R  L     S  K  V  A  P  V  I  K  A  R
     TGGAAGACAATGAAGAGAGAATGAGCCGCCTCTCAAAGGTGGCGCCAGTGATTAAAGCCA
                    1630                    1650                    1670
     M  M  E  Y  G  T  M  V  S     Y  Q  P  L  G  D  K  V  N  F
     GAATGATGGAGTATGGGACCATGGTCAGTCAGCTACCAACCCTTAGGAGATAAGGTCAACT
                    1690                    1710                    1730
     F  R  M  V  I  S  N  P  A     A  T  H  Q  D  I  D  F  L  I  E
     TCTTCCGCATGGTCATCTCAAACCCTGCAGCAACTCACCAAGACATTGACTTCCTCATTG
                    1750                    1770                    1790
     E  I  E  R  L  G  Q  D  L  *
     AAGAAATCGAACGCCTGGGACAAGATTTGTAATCACTTTGCTCACCAAACTTTCAGTTCT
                    1810                    1830                    1850
     CTAGGTAGACAGCTAAGTTGTCACAAACTGTGTAAATGTATTTGTAGTTTGTTCCAGAGT
                    1870                    1890                    1910
     AATTCTATTTCTATATCGTGGTGTCACAGTAGAGTCCAGTTTAAAA
                    1930                    1950
```

FIG. 2C

```
                                                                M   A   S
AGCTCGCCCGCAGCTCGCACTCGCAGGCGACCTGCTCCAAAGCCGATGGCATC
                                                            50
  P   G   S   G   F   W   S   F   G   S   E   D   G   S   G   D   S   E   N   P
TCCGGGCTCTGGCTTTTGGTCTTTTCGGGTCGGAAGATGGCTCTGGGGATTCCGAGAATCC
              70                              90                             110
  G   T   A   R   A   W   C   Q   V   A   Q   K   F   T   G   G   I   G   N   K
CGGCACAGGCGGAGCTTGGTGCCAAGTGGCTCAGAAGTTCACGGGCGGCATCGGAAACAA
             130                             150                             170
  L   C   A   L   L   Y   G   D   A   E   K   P   A   E   S   G   G   S   Q   P
ACTGTGCGCCCTGCTCTACGGAGACGCCGAGAAGCCGGAGAGCGGGGGAAGCCAACC
             190                             210                             230
  P   R   A   A   R   K   A   A   C   D   Q   K   P   C   S   C   S
CCCGCGGGCCGCCGGAAGGCCGCCTGCGACCAGAAGCCCTGCAGCTGCTC
             250                             270                             290
  K   V   D   V   N   Y   A   F   L   H   A   T   D   L   L   P   A   C   D   G
CAAAGTGGATGTCAACTACGCGTTTCTCCATGCAACAGACCTGCTGCCGGCGTGTGATGG
             310                             330                             350
  E   R   P   T   L   A   F   L   Q   D   V   M   N   I   L   L   Q   Y   V   V
AGAAAGGCCCACTTTGGCGTTTCTGCAAGATGTTATGAACATTTTACTTCAGTATGTGGT
             370                             390                             410
  K   S   F   D   R   S   T   K   V   I   D   F   H   Y   P   N   L   E   E   L   L   Q
GAAAAGTTTCGATAGATCAACCAAAGTTATTGATTTCCATTATCCTAATGAGCTTCCA
             430                             450                             470
  E   Y   N   W   E   L   A   D   Q   P   Q   N   L   E   E   I   M   H   C
AGAATATAATTGGGAATTGGCAGACCAACCACAAAATTTGGAGGAAATTTGATGCATTG
             490                             510                             530
  Q   T   L   K   Y   A   I   K   T   G   H   P   R   Y   F   N   Q   L   S
CCAAACAACTCTAAAAATATGCAATTAAAAACAGGGCATCCTAGATACTTCAATCAACTTTC
             550                             570                             590
  T   G   L   D   M   V   G   L   A   A   D   W   L   T   S   T   A   N   T   N
TACTGGTTTGGATATGGTTGGATTAGCAGCAGACTGGCTGACATCAACAGCAAATACTAA
```

FIG. 3A

```
       M  F  T  Y  E  I  A  P  V  F  V  L  L  E  Y  V  T  L  K  K
      CATGTTCACCTATGAAATTGCTCCAGTATTTGTGCTTTTGGAATATGTCACACTAAAGAA
       610                   630                   650
           670                   690                   710
       M  R  E  I  G  W  P  G  G  S  G  D  G  I  F  S  P  G  G
      AATGAGAGAAATCATTGGCTGGCCAGGGGGCTCTGGGGATGGGATATTTTCTCCCGGTGG
               730                   750                   770
       A  I  S  N  M  Y  A  M  M  I  A  R  F  K  M  F  P  E  V  K
      CGCCATATCTAACATGTATGCCATGATGATCGCACGCTTTAAGATGTTCCCAGAAGTCAA
           790                   810                   830
       E  K  G  M  A  A  L  P  R  L  I  A  F  T  S  E  H  S  H  F
      GGAGAAAGGAATGGCTGCTCTTCCCAGGCTCATTGCCTTCACGTCTGAACATAGTCATTT
               850                   870                   890
       S  L  K  K  G  A  A  A  L  G  I  G  T  D  S  V  I  L  I  K
      TTCTCTCAAGAAGGGAGCTGCAGCCTTAGGGATTGGAACAGACAGCGTGATTCTGATTAA
           910                   930                   950
       C  D  E  R  G  K  M  I  P  S  D  L  E  R  R  I  L  E  A  K
      ATGTGATGAGAGAGGGAAAATGATTCCATCTGATCTTGAAAGAAGGATTCTTGAAGCCAA
               970                   990                  1010
       Q  K  G  F  V  P  F  L  V  S  A  T  A  G  T  T  V  Y  G  A
      ACAGAAAGGGTTTGTTCCTTTCCTTGTCTCGGAGTGCCACAGCTGGAACCACCGTGTACGGAGC
           1030                  1050                  1070
       F  D  P  L  L  A  V  A  D  I  C  K  K  Y  K  I  W  M  H  V
      ATTTGACCCCCTCTTAGCTGTCGCTGACATTTGCAAAAAGTATAAGATCTGGATGCATGT
               1090                  1110                  1130
       D  A  W  G  G  G  L  L  M  S  R  K  H  K  W  K  L  S  G
      GGATGCAGCTTGGGGGTGGGGGATTACTGATGTCCGAAAACACAAGTGGAAACTGAGTGG
           1150                  1170                  1190
       V  E  R  A  N  S  V  T  W  N  P  H  K  M  M  G  V  P  L  Q
      CGTGGAGAGGGCCAACTCTGTGACGTGGAATCCACACAAGATGATGGGAGTCCCTTTGCA
```

FIG. 3B

```
      1210                   1230                   1250
   C   S   A   L   L   V   R   E   E   G   L   M   Q   N   C   N   Q   M   H   A
GTGCTCTGCTCTCCTGGTTAGAGAGAAGAGGGATTGATGCAGAACTGCAACCAAATGCATGC
      1270                   1290                   1310
   S   Y   L   F   Q   Q   D   K   H   Y   D   L   S   Y   D   T   G   D   K   A
CTCCTACCTCTTTCAGCAAGATAAACATTATGACCTGTCCTATGACACTGGAGACAAGGC
      1330                   1350                   1370
   L   Q   C   G   R   H   V   D   V   F   K   L   W   L   M   W   R   A   K   G
CTTACAGTGCGGGACGGCCACGTTGATGTTTTAAACTATGGCTGATGTGGAGGGCAAAGGG
      1390                   1410                   1430
   T   G   F   E   A   H   V   D   K   C   L   E   L   A   E   Y   L   Y   N
GACTACCGGGTTTGAAGCGCATGTTGATAAATGTTTGGAGTTGGCAGAGTATTTATACAA
      1450                   1470                   1490
   I   I   K   N   R   E   G   Y   E   M   V   F   D   G   K   P   Q   H   T   N
CATCATAAAAAACCGAGAAGGATATGAGATGGTGTTTGATGGGAAGCCTCAGCACACAAA
```

FIG. 3C

```
                                              V   C   F   W   Y   I   P   P   S   L   R   T   L   E   D   N   E   E   R   M
                                           TGTCTGCTTCTGGTACATTCCTCCAAGCTTGCGTACTCTGGAAGACAATGAAGAGAGAAT
                                                1570                      1590                      1610
     S   R   L   S   K   V   A   P   V   I   K   A   R   M   M   E   Y   G   T   T
  GAGTCGCCTCTCGAAGGTGGCTCCAGTGATTAAAGCCAGAATGATGGAGTATGGAACCAC
                    1630                      1650                      1670
     M   V   S   Y   Q   P   L   G   D   K   V   N   F   F   R   M   V   I   S   N
  AATGGTCAGTACCAACCCTTGGGAGACAAGGTCAATTTCTTCCGCATGGTCATCTCAAA
                    1690                      1710                      1730
     P   A   A   T   H   Q   D   I   D   F   L   I   E   E   I   E   R   L   G   Q
  CCCAGCGGCAACTCACCAAGACATTGACTTCCTGATTGAAGAAATAAAACGCCTTGGACA
                    1750                      1770                      1790
     D   L   *
  AGATTTATAATAACCCTTGCTCACCAAGCTGTTCCACTTCTCTAGGTAGACAATTAAGTTG
                    1810                      1830                      1850
  TCACAAACTGTGTGAATGTATTTGTAGTTTGTTCCAAAGTAAATCTATTTCTATATTGTG
                    1870                      1890                      1910
  GTGTCAAAGTAGAGTTTAAAAATTAAACAAAAAGACATTGCTCCTTTTAAAAGTCCTTT
                    1930                      1950                      1970
  CTTAAGTTTAGAATACCTCTCTAAGAATTCGTGACAAAAGGCTATGTTCTAATCAATAAG
                    1990                      2010                      2030
  GAAAAGCTTAAAAATTGTTATAAATACTTCCCTTACTTTTAATATAGTGTGCAAAGCAAAC
                    2050                      2070                      2090
```

FIG. 3D

```
GAP WEIGHT: 3.000      LENGTH WEIGHT: 0.100      QUALITY: 856.2    RATIO: 1.464
PERCENT SIMILARITY: 97.436       4817, PEP HGT2.PEP
AVERAGE MATCH: 0.540   AVERAGE MISMATCH: -0.396       LENGTH: 585    GAPS: 0
PERCENT IDENTITY: 96.068    AUGUST 22, 1990 08:20 **

1 MASPGSGFWSFGSEDGSGDPENPPTARAWCQVAQKFTGGIGNKLCALLYG  50
    ||||||||||||||||||| |||||||||||||||||||||||||||||
  1 MASPGSGFWSFGSEDGSGDSENPPTARAWCQVAQKFTGGIGNKLCALLYG  50

51 DSEKPAESGGSVTSRAATRKVACTCDQKPCSCPKGDVNYALLHATDLLPA 100
    |.|||||||| .|| ||||:|| || |||||.|.|:|||||||||||||
 51 DAEKPAESGGSQPPRAAARKAACACDQKPCSCSKVDVNYAFLHATDLLPA 100

101 CEGERPTLAFLQDVMNILLQYVVKSFDRSTKVIDFHYPNELLQEYNWELA 150
    |:|||||||||||||||||||||||||||||||||||||||||||||||
101 CDGERPTLAFLQDVMNILLQYVVKSFDRSTKVIDFHYPNELLQEYNWELA 150

151 DQPQNLEEILTHCQTTLKYAIKTGHPRYFNQLSTGLDMVGLAADWLTSTA 200
    ||||||||| .|||||||||||||||||||||||||||||||||||||
151 DQPQNLEEILMHCQTTLKYAIKTGHPRYFNQLSTGLDMVGLAADWLTSTA 200

201 NTNMFTYEIAPVFVLLEYVTLKKMREIIGWPGGSGDGIFSPGGAISNMYA 250
    |||||||||||||||||||||||||||||||||||||||||||||||||
201 NTNMFTYEIAPVFVLLEYVTLKKMREIIGWPGGSGDGIFSPGGAISNMYA 250

251 MLIARYKMFPEVKEKGMAAVPRLIAFTSEHSFSLKKGAAALGIGTDSVI  300
    |:||| ||||||||||||| |||||||||||||||||||||||||||||
251 MMIARFKMFPEVKEKGMAALPRLIAFTSEHSFSLKKGAAALGIGTDSVI  300

301 LIKCDERGKMIPSDLERRILEVKQKGFVPFLVSATAGTTVYGAFDPLLAV 350
    |||||||||||||||||||||.|||||||||||||||||||||||||||
301 LIKCDERGKMIPSDLERRILEAKQKGFVPFLVSATAGTTVYGAFDPLLAV 350

351 ADICKKYKIWMHVDAAWGGGLLMSRKHKWKLNGVERANSVTWNPHKMMGV 400
    ||||||||||||||||||||||||||||||||.|||||||||||||||
351 ADICKKYKIWMHVDAAWGGGLLMSRKHKWKLSGVERANSVTWNPHKMMGV 400
```

FIG. 4A

```
401 PLQCSALLVREEGLMQSCNQMHASYLFQQDKHYDLSYDTGDKALQCGRHV 450
    |||||||||||||||||||||||||||||||||||||||||||||||||
401 PLQCSALLVREEGLMQNCNQMHASYLFQQDKHYDLSYDTGDKALQCGRHV 450

451 DVFKLWLMWRAKGTTGFEAHIDKCLELAEYLYNIIKNREGYEMVFDGKPQ 500
    ||||||||||||||||||||:||||||||||||||||||||||||||||
451 DVFKLWLMWRAKGTTGFEAHVDKCLELAEYLYNIIKNREGYEMVFDGKPQ 500

501 HTNVCFWFVPPSLRVLEDNEERMSRLSKVAPVIKARMMEYGTTMVSYQPL 550
    ||||||||::|||||||||||||||||||||||||||||||||||||||
501 HTNVCFWYIPPSLRTLEDNEERMSRLSKVAPVIKARMMEYGTTMVSYQPL 550

551 GDKVNFFRMVISNPAATHQDIDFLIEEIERLGQDL 585
    ||||||||||||||||||||||||||||||||||
551 GDKVNFFRMVISNPAATHQDIDFLIEEIERLGQDL 585
```

FIG. 4B

CLONED GLUTAMIC ACID DECARBOXYLASE

This application is a divisional, of application Ser. No. 07/586,536, filed Sep. 21, 1990.

The present invention was supported by Grant NS22256 from the National Institutes of Health. The U.S. Government has certain rights in this invention.

BACKGROUND OF THE INVENTION

1. Field of the Invention

The present invention relates to the use of recombinant DNA technology for the transformation of a host organism with glutamic acid decarboxylase$_{65}$ (GAD$_{65}$) for the expression of GAD$_{65}$ polypeptides. Also encompassed are methods of using GAD$_{65}$ polypeptides diagnostically and therapeutically in autoimmune disease.

2. Description of the Background Art

Insulin-ependent diabetes mellitus (IDDM; type I diabetes) is one of the most common metabolic disorders. In the United States, IDDM affects approximately one in 300 to 400 people, and epidemiological studies suggest that its Incidence is increasing. The disease results from the autoimmune destruction of the insulin-producing β-cells of the pancreas. More specifically, the preonset stage is characterized by "insulitis", in which lymphocytes infiltrate the pancreatic islets and selectively destroy the β-cells. The typical IDDM presentation of hyperglycemia appears only after at least 80% of the insulin-producing β-cells are lost. The remaining β-cells are destroyed during the next few years.

Although insulin therapy allows most IDDM patients to lead normal lives, this replacement is imperfect and does not completely restore metabolic homeostasis. Thus, severe complications which result in dysfunctions of the eye, kidney, heart, and other organs are common in IDDM patients undergoing insulin therapy. Because of this, it is highly desirable to extend the latency period (e.g., through administration of immunosuppressant drugs) between the start of β-cell destruction and the actual requirement of insulin replacement (i.e., when 80% of the β-cells are destroyed). Therefore, a diagnostic test which determines the beginning of β-cell destruction would allow the clinician to administer immunosuppressant drugs (Silverstein, et al., *New England Journal of Medicine*, 319:599–604,1988) to extend this latency period and thus significantly delay the onset of insulin replacement side effects.

Many IDDM patients have sera which contain antibodies to a 64 kD molecule (Baekkeskov, et al., *J. Clin. Ivest.*, 79:926–934, 1987; Atkinson, et al., *Lancet*, 335:1357–1360, 1990), to islet cell cytoplasmic (ICA) molecules or islet cell surface (ICSA) molecules (Bottazzo, et al, Lancet, 1:668–672, 1980), or to insulin (Palmer, et al., *Science*, 222:1137–1139, 1983; Atkinson, et al., *Diabetes*, 35:894–898, 1986). Atkinson and coworkers (Atkinson, et al., *Lancet*, 335:1357–1360, 1990) have demonstrated that the presence of antibodies to the 64 kD molecule in human sera appears to be the earliest and most reliable indicator that onset of IDDM symptoms will eventually occur.

Recently, Baekkeskov and coworkers established that the 64 kD molecule and glutamic acid decarboxylase (GAD) have several antigenic epitopes in common and thus they may be identical or very similar molecules. Although this identification is an important finding, the use of this information as a diagnostic tool for predicting IDDM is quite cumbersome and limited unless knowledge of the molecular biology of GAD is known. Consequently, the cloning and subsequent production of large quantities of the 64 kD molecule, or a GAD molecule which is antigenically substantially identical to the 64 kD molecule, will allow the development of a diagnostic kit designed to predict IDDM. The present invention provides a means for accomplishing this result.

SUMMARY OF THE INVENTION

The present invention arose out of the discovery that recombinant DNA technology could be used to produce eukaryotic GAD$_{65}$ polypeptide and that GAD$_{65}$ polypeptide could be used in the diagnosis and therapy of patients with autoimmune disease. Particularly relevant is the use of cloned eukaryotic GAD$_{65}$ polypeptide in the diagnosis of patients having, or at risk of having, insulin-dependent diabetes mellitus (IDDM).

A major advantage of the present invention is that it provides the art with a ready source of eukaryotic GAD$_{65}$ polypeptide corresponding to that purified from natural sources, while avoiding the problems associated with the isolation of naturally occurring eukaryotic GAD$_{65}$ polypeptide when separating it from other eukaryotic non-GAD$_{65}$ polypeptides. This absence of other eukaryotic non-GAD$_{65}$ polypeptides is significant in that it allows the development of test systems which will only detect antibodies specifically reactive with GAD$_{65}$ polypeptides.

Another advantage of providing eukaryotic GAD$_{65}$ polypeptide in host cells is that by so doing, it is possible to obtain much larger quantities of the polypeptide than are currently practicably available from natural sources. As a consequence, not only is it possible to use the polypeptide of the invention to more accurately classify patients with such autoimmune diseases as IDDM, but it is also now possible to provide commercially useful quantities of GAD$_{65}$ polypeptide for use in diagnostic systems.

DESCRIPTION OF THE DRAWINGS

FIG. 2 DNA sequence and corresponding amino acid sequence for rat GAD$_{65}$.

FIG. 3 DNA sequence and corresponding amino acid sequence for human GAD$_{65}$.

FIG. 4 Comparison of rat GAD$_{65}$ and human GAD$_{65}$ amino acid sequences.

DETAILED DESCRIPTION OF THE INVENTION

Figure 1:
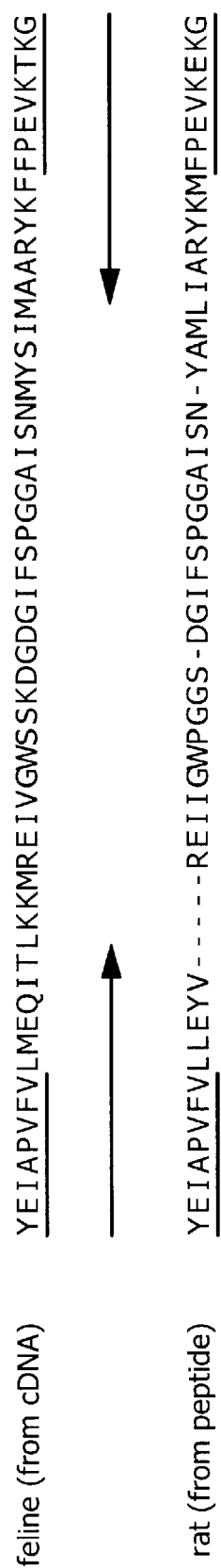
FIG. 1 Cloning strategy for obtaining GAD$_{65}$ and GAD$_{67}$ specific cDNA probes.

The present invention relates to the manipulation of genetic materials by recombinant procedures which make possible the production of polypeptides possessing part or all of the primary structural conformation for one or more of the epitopes for binding autoantibodies to glutamic acid decarboxylase$_{65}$ (GAD$_{65}$). These polypeptides are highly useful for the immunological detection of autoantibodies reactive with them, since such autoantibodies are indicative of autoimmune diseases such as insulin dependent diabetes mellitus and "stiff man" syndrome. These polypeptides can also be used for purposes of screening drugs, such as those that alter GAD function, and for generation of polyclonal and monoclonal antibodies which, in turn, can be used diagnostically to detect $GAD_{65}$.

The development of specific DNA sequences encoding eukaryotic $GAD_{65}$ polypeptide for splicing into DNA vectors can be accomplished using a variety of techniques. For example, alternative methods which can be employed include (1) the isolation of a double stranded DNA sequence from the genomic DNA of the eukaryote; (2) the chemical manufacture of a DNA sequence to provide the necessary codons for the polypeptide of interest; and (3) the in vitro synthesis of a double stranded DNA sequence by reverse transcription of mRNA isolated from a eukaryotic donor cell. In the latter case, a double stranded DNA complement of mRNA is eventually formed which is generally referred to as cDNA.

The manufacture of DNA sequences is frequently the method of choice when the entire sequence of amino acid residues of the desired polypeptide product is known. When the entire sequence of amino acid residues of the desired polypeptide is not known, the direct manufacture of DNA sequences is not possible and the method of choice is the formation of cDNA sequences. Among the standard procedures for isolating cDNA sequences of interest is the formation of plasmid-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double stranded DNA or RNA probe sequences duplicating a sequence putatively present in the target cDNA may be employed in DNA/DNA hybridization procedures which are carried out on cloned copies of the cDNA which have been denatured into a single stranded form (Jay, et al., *Nucleic Acid Research*, 11:2325, 1983).

Hybridization procedures are useful for the screening of recombinant clones by using labeled mixed synthetic oligonucleotide probes wherein each is potentially the complete complement of a specific DNA sequence in the hybridization sample which includes a heterogeneous mixture of denatured double stranded DNA. For such screening, hybridization is preferably performed on either single stranded DNA or denatured double stranded DNA. These procedures are particularly useful in the detection of cDNA clones derived from sources where an extremely low amount of mRNA sequences relating to the polypeptide of interest are present. In other words, by using stringent hybridization conditions directed toward avoidance of non-specific binding, it is possible, for example, to allow the autoradiographic visualization of a specific cDNA clone by the hybridization of the target DNA to that single probe in the mixture which is its complete complement (Wallace, et al., *Nucleic Acid Research*, 9:879, 1981).

In addition, a GAD cDNA library can be screened by injecting the various cDNAs into oocytes, allowing sufficient time for expression of the cDNA gene products to occur, and testing for the presence of the desired cDNA expression product, for example, by using antibody specific for $GAD_{65}$ polypeptide or by using functional assays for $GAD_{65}$ enzymatic activity.

Alternatively, a cDNA library can be screened indirectly for $GAD_{65}$ peptides having at least one epitope using antibodies to $GAD_{65}$ (Chang and Gottlieb, *J. Neurosci.*, 8:2123, 1988). Such antibodies can be either polyclonally or monoclonally derived and used to detect expression product indicative of the presence of $GAD_{65}$ cDNA. Preferred are antibodies directed to an epitope found in the first 100 amino acids of the N-terminal portion of $GAD_{65}$.

Of the three above-noted methods for developing specific DNA sequences for use in recombinant procedures, the use of genomic DNA isolates, is the least common This is especially true when it is desirable to obtain the microbial expression of mammalian polypeptides because of the presence of introns.

The present invention provides novel polypeptides of $GAD_{65}$ which have part or all of the primary structural conformation, that is, a continuous sequence of amino acid residues, having at least one epitope for antibodies to $GAD_{65}$.

It is possible to use the polypeptide fragments of the invention rather than intact $GAD_{65}$ to detect autoantibodies to $GAD_{65}$. The term "polypeptide," as applied to $GAD_{65}$ polypeptide, denotes any sequence of amino acids having an epitope for autoantibodies to $GAD_{65}$, wherein the sequence of amino acids is encoded by all or part of the cDNA sequences of the invention.

The polypeptides resulting from microbial expression of the DNA sequences of the invention can be further characterized by their freedom from association with other eukaryotic polypeptides or other contaminants which might otherwise be associated with $GAD_{65}$ in its natural cellular environment or in such extracellular fluids as plasma or urine.

Studies by the present inventors unequivocally establish that $GAD_{65}$ and $GAD_{67}$ are encoded by distinct genes and are not produced, for example, by post-transcriptional or post-translational modification of a common genomic sequence. Evidence proving that $GAD_{65}$ and $GAD_{67}$ are encoded by different genes include: (a) the largest contiguous sequence of exact identity between $GAD_{65}$ and $GAD_{67}$ cDNAs is only 17 nucleotides in length, (b) cDNAs from $GAD_{65}$ and $GAD_{67}$ do not cross hybridize with each other's or with each other's mRNA under low stringency conditions (2.0×SSC, 0.01% SDS, 23° C.), and (c) $GAD_{65}$ and $GAD_{67}$ cDNAs do not cross hybridize with isolated genomic clones encoding $GAD_{67}$ and $GAD_{65}$, respectively.

The term "host" is meant to include not only prokaryotes, but also such eukaryotes as yeast, filamentous fungi, as well as plant and animal cells which can replicate and express an intron-free DNA sequence of eukaryotic $GAD_{65}$. However, prokaryotes are preferred as the host organism.

The term "prokaryotes" is meant to include all bacteria which can be transformed or transfected with the gene for the expression of $GAD_{65}$. Prokaryotic hosts may include gram negative as well as gram positive bacteria such as, for example, *E. coli, S. typhimurium, Serratia marcescens* and *Bacillus subtilis.*

A recombinant DNA molecule coding for the $GAD_{65}$ polypeptides can be used to transform or transfect the host using any of the techniques commonly known to those of ordinary skill in the art. Especially preferred is the use of a plasmid or a virus containing the $GAD_{65}$ coding sequence for purposes of prokaryotic transformation or transfection, respectively.

Methods for preparing fused, operably linked genes and expressing them in bacteria are well-known in the art (Maniatis, et al., *Molecular Cloning: A Laboratory Manual*, Cold Spring Harbor Laboratory, Cold Spring Harbor, N.Y., 1989). The genetic constructs and methods described therein can be utilized for expression of $GAD_{65}$ in prokaryotic hosts.

In general, expression vectors containing promotor sequences which facilitate the efficient transcription of the inserted eukaryotic genetic sequence are used in connection with the host. The expression vector typically contains an origin of replication, a promoter, and a terminator, as well as specific genes which are capable of providing phenotypic selection of the transformed cells. The transformed prokaryotic hosts can be grown in fermentors and cultured according to techniques known in the art to achieve optimal cell growth. The polypeptides of the invention can then be isolated from the grown medium, cellular lysates, or cellular membrane fractions.

The isolation and purification of the microbially expressed polypeptides of the invention may be by any conventional means such as, for example, preparative chromatographic separations and immunological separations such as those involving the use of monoclonal or polyclonal antibody.

By having provided the sequence of amino acid residues of $GAD_{65}$, the present invention provides for the manufacture of DNA sequences which code for the host expression of polypeptide analogs or derivatives of $GAD_{65}$ which differ from naturally-occurring forms in terms of the identity or location of one or more amino acid residues and which share some or all of the epitopes of naturally-occurring polypeptide forms.

The novel DNA sequences of the invention include all sequences useful in providing the expression in prokaryotic or eukaryotic host cells of polypeptides which have at least a part of the primary structural conformation for one or more epitopes capable of reacting with autoantibodies to $GAD_{65}$ which are comprehended by: (a) the DNA sequence as set forth in FIG. 2 or 3 or their complementary strands; (b) DNA sequences which hybridize to DNA sequences defined in (a) or fragments thereof; and (c) DNA sequences which, but for the degeneracy of the genetic code, would hybridize to DNA sequences defined in (a) and (b) above. Specifically comprehended in (b) are genomic DNA sequences which encode allelic variant forms of $GAD_{65}$. Part (c) specifically comprehends the manufacture of DNA sequences which encode $GAD_{65}$, $GAD_{65}$ fragments, and $GAD_{65}$ analogs wherein the DNA sequences thereof may incorporate codons which facilitate translation of mRNA in non-vertebrate hosts.

Since the cDNA sequence of the invention encodes essentially the entire human or rat $GAD_{65}$ molecule, it is now a matter of routine to prepare, subclone, and express smaller polypeptide fragments of cDNA from this or a corresponding cDNA sequence which would encode as few as one epitope for autoantibodies to human or rat $GAD_{65}$. The presence of such an epitope on a cloned polypeptide can then be confirmed using, for example, sera from a patient with autoantibodies to $GAD_{65}$. An example of such a smaller peptide is the first approximately 100 amino acids from the N-terminus of $GAD_{65}$ (shown in FIG. 3). This amino acid sequence is essentially absent from $GAD_{67}$.

The $GAD_{65}$ of the invention is particularly suited for use in immunoassays in which it can be utilized in liquid phase or bound to a solid phase carrier. In addition, $GAD_{65}$ used in these assays can be detectably labeled in various ways.

Examples of immunoassays which can utilize the $GAD_{65}$ of the invention are competitive and non-competitive immunoassays in either a direct or indirect format. Examples of such immunoassays are the radioimmunoassay (RIA), the sandwich (immunometric assay) and the Western blot assay. Detection of antibodies which bind to the $GAD_{65}$ of the invention can be done utilizing immunoassays which run in either the forward, reverse, or simultaneous modes, including immunohistochemical assays on physiological samples. The concentration of $GAD_{65}$ which is used will vary depending on the type of immunoassay and nature of the detectable label which is used. However, regardless of the type of immunoassay which is used, the concentration of $GAD_{65}$ utilized can be readily determined by one of ordinary skill in the art using routine experimentation.

The $GAD_{65}$ of the invention can be bound to many different carriers and used to detect the presence of antibody specifically reactive with the polypeptide. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding $GAD_{65}$, or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

Alternatively, the polypeptide of the invention can be used to detect antibodies to $GAD_{65}$ by measuring GAD enzymatic activity. For example, $GAD_{65}$ and a specimen suspected of having antibodies to $GAD_{65}$ can be incubated for a period of time and under conditions sufficient to allow binding to occur between $GAD_{65}$ and the antibodies. The reaction product is precipitated and then tested for GAD enzymatic activity.

For purposes of the invention, the antibody which binds to $GAD_{65}$ of the invention may be present in various biological fluids and tissues. Any sample containing a detectable amount of antibodies to $GAD_{65}$ can be used. Normally, a sample is a liquid such as urine, saliva, cerebrospinal fluid, blood, serum and the like, or a solid or semi-solid such as tissue, feces and the like.

The materials for use in the assay of the invention are ideally suited for the preparation of a kit. Such a kit may comprise a carrier means being compartmentalized to receive in close confinement one or more container means such as vials, tubes and the like, each of the container means comprising one of the separate elements to be used in the method. For example, one of the container means may comprise $GAD_{65}$ bound to a carrier. A second container may comprise soluble, detectably-labeled second antibody, in lyophilized form or in solution.

In addition, the carrier means may also contain a plurality of containers each of which comprises different, predetermined amounts of $GAD_6$. These latter containers can then be used to prepare a standard curve into which can be interpolated the results obtained from the sample containing the unknown amount of autoantibodies to $GAD_{65}$.

In using the kit all the user has to do is add, to a container, a premeasured amount of a sample containing a measurable, yet unknown amount of autoantibodies to $GAD_{65}$ to be detected, a premeasured amount of carrier-bound $GAD_{65}$ present in the first container, and a premeasured amount of the detectably labeled second antibody present in the second container. Alternatively, the non-detectably labeled $GAD_{65}$ can be provided attached to the container to which the sample and the detectably labeled second antibody are added. After an appropriate time for incubation, an immune complex is formed and is separated from the supernatant fluid, and the immune complex or the supernatant fluid are detected, as by radioactive counting or addition of an enzyme substrate, and color development.

The term "ameliorate" denotes a lessening of the detrimental effect of the autoimmune response in the patient receiving therapy. The term "therapeutically effective" means that the amount of $GAD_{65}$ polypeptide used is of sufficient quantity to ameliorate the cause of disease due to the autoimmune response.

The recombinant $GAD_{65}$ polypeptides of the invention can also be used therapeutically in patients having an autoimmune response to $GAD_{65}$. Such therapy can be accomplished by, for example, the administration of recombinant $GAD_{65}$ polypeptide. Such administration can utilize unlabeled as well as labeled $GAD_{65}$ polypeptide. When unlabeled $GAD_{65}$ polypeptide is utilized advantageously, it would be in a form wherein, for example, the $GAD_{65}$ polypeptides are in fragments which are too small to stimulate an immune response, but large enough to bind, or block, the continuance of the autoimmune response. For example, $GAD_{65}$ could be digested enzymatically into epitope-sized peptides (typically 5–12 amino acids in length) and thereby bind to Fab binding portions present in the body fluids, or on the surface of immune cells, of the patient with autoimmune disease.

Alternatively, the recombinant $GAD_{65}$ polypeptides of the invention could be administered labeled with a therapeutic agent. These agents can be coupled either directly or indirectly to the $GAD_{65}$ polypeptides of the invention. One example of indirect coupling is by use of a spacer moiety. These spacer moieties, in turn, can be either insoluble or soluble (Diener, et al., Science, 231:148, 1986) and can be selected to enable drug release from the $GAD_{65}$ polypeptide at the target site. Examples of therapeutic agents which can be coupled to the $GAD_{65}$ polypeptides of the invention for immunotherapy are drugs, radioisotopes, lectins, and toxins.

The drugs with which can be conjugated to the $GAD_{65}$ polypeptides of the invention include compounds which are classically referred to as drugs such as mitomycin C, daunorubicin, and vinblastine.

In using radioisotopically conjugated $GAD_{65}$ polypeptides of the invention for immunotherapy, certain isotopes may be more preferable than others depending on such factors as leukocyte distribution as well as stability and emission. Depending on the autoimmune response, some emitters may be preferable to others. In general, $\alpha$ and $\beta$ particle-emitting radioisotopes are preferred in immunotherapy. Preferred are short range, high energy $\alpha$ emitters such as $^{212}Bi$. Examples of radioisotopes which can be bound to the $GAD_{65}$ polypeptides of the invention for therapeutic purposes are $^{125}I$, $^{131}I$, $^{90}Y$, $^{67}Cu$, $^{212}Bi$, $^{211}At$, $^{212}Pb$, $^{47}Sc$, $^{109}Pd$ and $^{188}Re$.

Lectins are proteins, usually isolated from plant material, which bind to specific sugar moieties. Many lectins are also able to agglutinate cells and stimulate lymphocytes. However, ricin is a toxic lectin which has been used immunotherapeutically. This is accomplished by binding the $\alpha$-peptide chain of ricin, which is responsible for toxicity, to the antibody molecule to enable site specific delivery of the toxic effect.

Toxins are poisonous substances produced by plants, animals, or microorganisms that, in sufficient dose, are often lethal. Diphtheria toxin is a substance produced by *Corynebacterium diphtheria* which can be used therapeutically. This toxin consists of an $\alpha$ and $\beta$ subunit which under proper conditions can be separated. The toxic A component can be bound to $GAD_{65}$ polypeptide and used for site specific delivery to a leukocyte expressing a receptor for $GAD_{65}$ polypeptide.

Other therapeutic agents which can be coupled to the $GAD_{65}$ polypeptides of the invention, as well as ex vivo and in vivo therapeutic protocols, are known, or can be easily ascertained, by those of ordinary skill in the art.

The dosage ranges for the administration of the $GAD_{65}$ polypeptides of the invention are those large enough to produce the desired effect in which the symptoms or cellular destruction of the autoimmune response are ameliorated. The dosage should not be so large as to cause adverse side effects, such as unwanted cross-reactions, anaphylactic reactions, and the like. Generally, the dosage will vary with the age, condition, sex, and extent of the disease in the patient and can be determined by one of skill in the art. The dosage can be adjusted by the individual physician in the event of any counterindications. Dosage can vary from about 0.1 $mg/M^2$ to about 2000 $mg/m^2$, preferably about 0.1 $mg/m^2$ to about 500 $mg/m^2$/dose, in one or more dose administrations daily, for one or several days.

The $GAD_{65}$ polypeptides of the invention can be administered parenterally by injection or by gradual perfusion over time. The $GAD_{65}$ polypeptides of the invention can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention also relates to a method for preparing a medicament or pharmaceutical composition comprising the $GAD_{65}$ polypeptides of the invention, the medicament being used for therapy of autoimmune response to $GAD_{65}$.

The above disclosure generally describes the present invention. A more complete understanding can be obtained by reference to the following specific examples which are provided herein for purposes of illustration only and are not intended to limit the scope of the invention.

EXAMPLE 1

CLONING AND EXPRESSION OF $GAD_{65}$

A. RECOMBINANT DNA PROCEDURES

In order to obtain cDNA probes specific for $GAD_{65}$ and $GAD_{67}$, total RNA was extracted from adult rat brain by guanidine isothiocyanate-cesium gradient using the method of Chirgwin, et al. (*Biochemistry*, 18:5294, 1979). Poly (A) RNA was purified on oligo dT cellulose, using the protocol by Bethesda Research Laboratories (BRL). First strand synthesis was performed by using MMLV-reverse transcriptase (BRL), with conditions suggested, except that poly d(N$_6$)-mers (Pharmacia) were used as primers. This cDNA-RNA mixture was heat inactivated at 65° C. for 15 min and stored at −20° C. For PCR, 1/50 of the sample was added to the 100 µl reaction. Degenerate oligonucleotides were synthesized (Applied Biosystems) to encode the underlined common amino acid sequences of feline (from cDNA) (Kobayashi, et al., *J. Neurosci.*, 7:2768, 1987) and rat (from peptides) (Chang and Gottlieb, *J. Neurosci.*, 8:2123, 1988) GAD (FIG. 1). The 5'-end sequence of each degenerate oligonucleotide contained one strand of the DNA sequence recognized by either SstI and HindIII (5' oligo) or SstI and SstII (3'-end oligo). These primers were used for selective amplification by polymerase chain reaction of the generated cDNA template as described by Gould, et al. (*Proc. Natl. Acad. Sci., USA*, 86:1934, 1989). PCR products were subcloned into HindIII/SstI double digested Bluescript SK vector (Stratagene), transformed into DH5 (BRL), and plated by standard methods (Maniatis, et al., *Molecular Cloning: A Laboratory Manual*, Cold Spring Harbor Laboratory, Cold Spring Harbor, N.Y., 1989).

Colony hybridization was done with an 5'-$^{32}$P end labeled oligonucleotide specific to feline GAD$_{67}$ (Kobayashi, et al., *J. Neurosci.*, 7:2768, 1987). End labeling of oligonucleotide, hybridization conditions, and washing conditions were done as described (Wallace, et al., in *Guide to Molecular Cloning Techniques*; Berger, et al., *Eds. in Methods of Enzymology*; Abelson, et al., Eds. Academic Press, Inc., San Diego, 432–442, 1987), except that the nitrocellulose filters were washed at 50° C. for 15 min. Colonies which were positive and negative in the hybridization were individually picked and grown overnight in Terrific Broth (Tartof, et al., *Focus*, 9:12, 1987). DNA was isolated using a boiling method (Maniatis, et al., *Molecular Cloning: A Laboratory Manual*, Cold Spring Harbor Laboratory, Cold Spring Harbor, N.Y., 1989) and templates were denatured by 0.2N NaOH and purified by Sephacryl S400 spun columns (Pharmacia). Sequencing of denatured double stranded template was by the chain-termination method (Sanger, et al., *Proc. Natl. Acad. Sci., USA*, 74:5463, 1977) using the T7-sequencing kit (Pharmacia).

As shown in FIG. 1, PCR-generated rat GAD$_{65}$ and GAD$_{67}$ cONAs were used as probes to screen a lambda ZAP (Stratagene) rat hippocampus library provided by S. Heinemann (Salk Institute) by standard techniques (Maniatis, et al., *Molecular Cloning: A Laboratory Manual*, Cold Spring Harbor Laboratory, Cold Spring Harbor, N.Y., 1989). A 2400 nucleotide GAD$_{65}$ cDNA (the largest clone) was isolated and subcloned by "zapping" as described by Stratagene. When a rat GAD$_{67}$ cDNA was obtained which was smaller than a 3.2 kb rat GAD$_{67}$ cONA clone already on hand, the larger cONA was sequenced. Exo III deletions (Henikoff, *Gene*, 28:351, 1984) were made in both directions for GAD$_{65}$ and GAD$_{67}$ and templates were prepared and sequenced as described above. Anchored PCR (Frohman, et al., *Proc. Natl. Acad. Sci., USA*, 85:8998, 1988) was done to clone the remaining 5'-ends of GAD$_{65}$ and GAD$_{67}$ mRNAs which were not represented in the original cDNA clones isolated in the library screening. Sequencing of these clones revealed that neither GAD$_{65}$ nor GAD$_{67}$ mRNAs contained any further initiation codons (AUGs) in frame with the previously designated initiation codons of the original cDNA clones.

EXAMPLE 2

CHARACTERIZATION OF CLONED GAD$_{65}$

A. NORTHERN BLOT HYBRIDIZATION

Two PCR-derived cDNA probes were hybridized to Northern blots containing rat brain RNA in order to determine whether the GAD$_{67}$ and GAD$_{65}$ cDNAs were derived from two different mRNAs. RNA was extracted as described in Example 1. Poly (A) RNA was separated by electrophoresis in formaldehyde and transferred onto Biotrans (ICN) membranes, and hybridization was performed as described by Well, et al. (*J. Neurosci.*, 16:31 1, 1986), except that 100 µl/ml of poly (A) was added. Probes were labeled to approximately 10$^9$ dpm/µg by the oligolabeling procedure of Feinberg and Vogelstein (*Anal. Biochem.*, 132:6,1983). Identical results were subsequently obtained with full-length clones of GAD$_{65}$ and GAD$_{67}$ cDNAs.

Figures 5, 6:
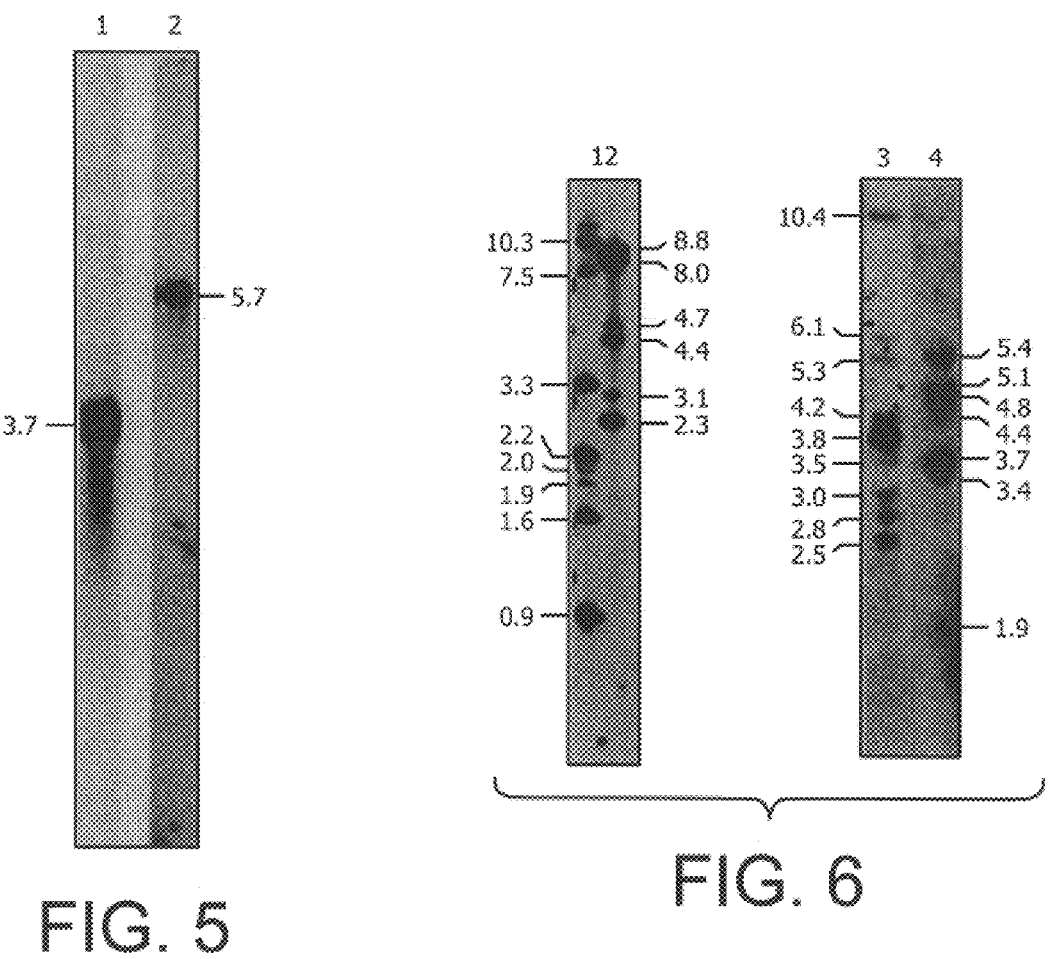
FIG. 5 GAD$_{65}$ and GAD$_{67}$ cDNAs hybridize to different size RNAs.
FIG. 6 Southern blots hybridized with cDNA probes specific for GAD$_{65}$ and GAD$_{67}$.

As shown in FIG. 5, lanes 1 and 2 contain 1 µg of poly (A) selected RNA extracted from rat cerebellum. Lane 1 was hybridized to a cDNA probe for the rat cognate of feline GAD$_{67}$ (Kobayashi, et al., *J. Neurosci.*, 7:2768, 1987) and lane 2 with a cDNA probe for the rat peptide sequence (which corresponds to GAD$_{65}$).

The cDNA probe for the rat peptide sequence hybridized to a 5.7 kb RNA, while the cDNA probe for the rat cognate of our feline cDNA, hybridized to a 3.7 kb RNA. This demonstrates that GAD$_{65}$ and GAD$_{67}$ are not derived from the same mRNA.

B. GENOMIC HYBRIDIZATION OF GAD$_{65}$ AND GAD$_{65}$

In order to investigate the possibility that GAD$_{67}$ and GAD$_{65}$ arise from separate genes, cDNAs of both GAD$_{67}$ and GAD$_{65}$ were hybridized to DNA blots containing genomic DNA.

For Southern blots, genomic DNA was extracted from rat liver as described (Kaiser, et al., in *DNA Cloning*, vol.I, A Practical Approach, D. M. Glover ed., IRL Press, Oxford, 38–40, 1985). DNA (10 µg/sample) was digested to completion with EcoRI and HindIII using conditions recommended by the suppliers (BRL, Gaithersburg, Md.). DNA fragments were separated by electrophoresis at 1.5 v/cm for 16 hrs in 0.8% agarose. The DNA was then transferred to Zeta-Probe membranes (Bio-Rad), hybridized, and washed, as described by Gatti, et al. (*Biotechniques*, 2:148, 1984), except that 5 µg/ml Carnation dried milk was substituted for Denhardt's solution. Probes for Southern blots were labeled as described in Example 1, above.

As shown in FIG. 6, genomic DNA digested with HindIII and EcoRI are in lanes 1 and 3 and lanes 2 and 4, respectively. GAD$_{67}$ cDNA was hybridized to lanes 1 and 2, whereas GAD$_{65}$ cDNA was hybridized to lanes 3 and 4. Numbers along the side of the gel are the DNA fragment sizes in kilobases.

This data shows that the two cDNAs hybridize to genomic fragments of different sizes. In addition, the greatest contiguous stretch of identical nucleotide sequence of GAD$_{65}$ and GAD$_{67}$ cDNAs is only 17 nucleotide bases in length. Thus, GAD$_{67}$ and GAD$_{65}$ are encoded by two distinct genes.

C. ENZYMATIC COMPARISON OF GAD$_{67}$ AND GAD$_{65}$

Studies were done comparing the effect of PLP on the activity of GAD$_{67}$ and GAD$_{65}$. In so doing, both cONAs were subcloned into vectors that allowed their expression in bacteria (Studier, et al., *J. Mol. Biol.*, 189:1 13, 1986). Overexpression of "fusionless" GAD$_{65}$ and GAD$_{67}$ was accomplished by subcloning GAD$_{65}$ cDNA into the NcoI site of pET-8c and GAD$_{67}$ cDNA into the NheI site of pET-Sc vectors (Studier, et al., *J. Mol. Biol.*, 189:1 13, 1986).

To obtain compatible sticky ends for correct in-frame subcloning of both cDNAs, selective amplification was performed by PCR using conditions suggested by United States Biochemical (USB), with 200 μM dNTPs and 1.5 mM $MgCl_2$ in the mixture and annealing at 55° C. with 20 cycles to decrease infidelity of AmpliTAQ (USB). Primers specific for $GAD_{65}$ and $GAD_{67}$ contained one DNA strand of the NcoI and SpeI recognition sites, respectively. Since there is a NheI restriction site within the coding region of $GAD_{67}$, SpeI (which is compatible with NheI) was used.

PCR products were subcloned into their respective pET vectors, transformed into DH5 and plated as described (Maniatis, et al., *Molecular Cloning: A Laboratory Manual*, Cold Spring Harbor Laboratory, Cold Spring Harbor, N.Y., 1989). Colonies were picked and grown overnight in LB broth with 50 μg/ml ampicillin. Subclones with correct orientation were transformed into BL21(DE3) strain (Studier, et al., *J. Mol. Biol.*, 189:113, 1986) for overexpression. As a negative control, the pET-8C vector with no insert was transformed and subsequently induced. Single colonies were picked, grown, induced by 1 mM isopropyl-B-D-thiogalacto-pyranoside (IPTG), and analyzed on SDS-PAGE gels as described (Sambrook, et al., *Molecular Cloning a Laboratory Manual*, Cold Spring Harbor Laboratory Press, Cold Spring Harbor, 17.15–17.16, 1989).

To measure GAD activity, we induced 10 ml cultures of bacteria at $OD_{600}$-0.5 with 1 mM IPTG. Two hours after induction, bacteria was spun down and resuspended and sonicated in 1 ml of homogenizing buffer (1 mM phenylmethylsulfonyl fluoride (PMSF), 1 mM 2-aminoethylisothiouronium bromide (AET), and 60 mM potassium phosphate, pH 7.1). After sonication, cell debris was removed by centrifugation and protein concentration was measured (Bradford, *Anal. Biochem.*, 72:248, 1986) in the supernatant (supernatant was stored in aliquots at –70° C.). Brain homogenates were prepared as described (Legay, et al., *J. Neurochem.*, 46:1478, 1986). GAD activity was measured as described (Krieger, et al., *J. Neurochem.*, 33:299, 1984) with 0.2 mM PLP present or absent and 20 μl of brain homogenate or bacterial lysate in the incubation mixture. Production of $^{14}CO_2$ in bacterial lysates was linear with respect to time of incubation and protein concentration.

| Source | GAD Specific Ativity[a] – PLP | GAD Specific Ativity[a] + PLP | Fold Increase in Induction |
|---|---|---|---|
| BL21(DE3) + pET-8c | 12 ± 0.4 | 9 ± 1 | — |
| BL21(DE3) + pET-$GAD_{65}$ | 115 ± 3 | 773 ± 61 | 6.7 |
| BL21(DE3) + pET-$GAD_{67}$ | 160 ± 2 | 389 ± 8 | 2.4 |
| Rat Brain | 131 ± 5 | 216 ± 2 | 1.6 |

[a]cpms of $^{14}CO_2$/μg protein/hr of triplicates ± S.E.M.

As shown in Table 1, bacterial lysates containing $GAD_{65}$ or $GAD_{67}$ catalyze the conversion of [1-$^{14}C$]-glutamate to GABA and $^{14}CO_2$.

PLP stimulates the enzymatic activity of $GAD_{65}$ more than $GAD_{67}$. This greater stimulation probably reflects the faster cycling of $GAD_{65}$ through the inactivation cycle proposed by Martin and coworkers (Martin, *Cell. Mol. Neurobiol.*, 7:237, 1987). This faster cycling suggests that $GAD_{65}$ contributes more to the pool of apo-GAD that exists in vivo (Miller, et al., *Brain Res. Bull.*, 5(Suppl.2):89, 1980). Thus, in vivo, PLP appears to regulate $GAD_{65}$ activity more than $GAD_{67}$ activity.

$GAD_{65}$ activity in bacterial lysates is similar to the five-fold PLP stimulation of GAD activity found in synaptosomes prepared from rat substantia nigra (Miller, et al., *J. Neurochem.*, 33:533, 1979). Because both GADs are more dependent upon added PLP in bacteria than is the GAD activity in crude rat brain homogenates, the endogenous PLP concentration of bacteria lysates may be less than rat brain homogenates.

D. IMMUNOLOGICAL IDENTIFICATION OF $GAD_{65}$ AND $GAD_{67}$

Rat brain homogenates and bacterial lysates were extracted as described above. Equal volumes of loading buffer were added to each sample as described (Harlow, et al., *Antibodies, A Laboratofy Manual*, Cold Spring Harbor Laboratory, Cold Spring Harbor, N.Y., 1988). Proteins were separated by electrophoresis in a 10% acrylamide gel in SDS and electrophoretically transferred to nitrocellulose (Harlow, et al., *Antibodies, A Laboratory Manual*, Cold Spring Harbor Laboratory, Cold Spring Harbor, N.Y., 1988). The unreacted sites were blocked with a phosphate buffered saline (PBS) solution containing 2% bovine serum albumin (fraction V), 1% gelatin, and 1% Triton-X-100 at 42° C. for one hr. After washing, the nitrocellulose filter was then cut into three sections and incubated with the following primary antibodies: lanes 1 to 4 with a 1/2000 dilution of the antiserum of Oertel, et al. (*Neuroscience*, 6:2689, 1981), which recognizes both $GAD_{67}$ and $GAD_{65}$; lanes 5–8 with a 1/2000 dilution of K-2 antiserum, which recognizes only $GAD_{67}$; lanes 9–12 with a 1/2000 dilution of GAD-6 monoclonal antibody, which is specific for $GAD_{65}$ (Chang, et al., *J. Neurosci.*, 8:2123, 1988). All filters were extensively washed and appropriate secondary antibodies were incubated and washed. Bound antibodies were detected with $^{125}I$-labeled protein A and autoradiography. Each lane contained the following: lanes 1, 5, and 9 are BL21(DE3)+pET-$GAD_{67}$; lanes 2, 6, and 10 are BL21(DE3)+pET-$GAD_{65}$; lanes 3, 7, and 11 are rat brain homogenate; and lanes 4, 8, and 12 are BL21(DE3)+pET-8c.

Figure 7:
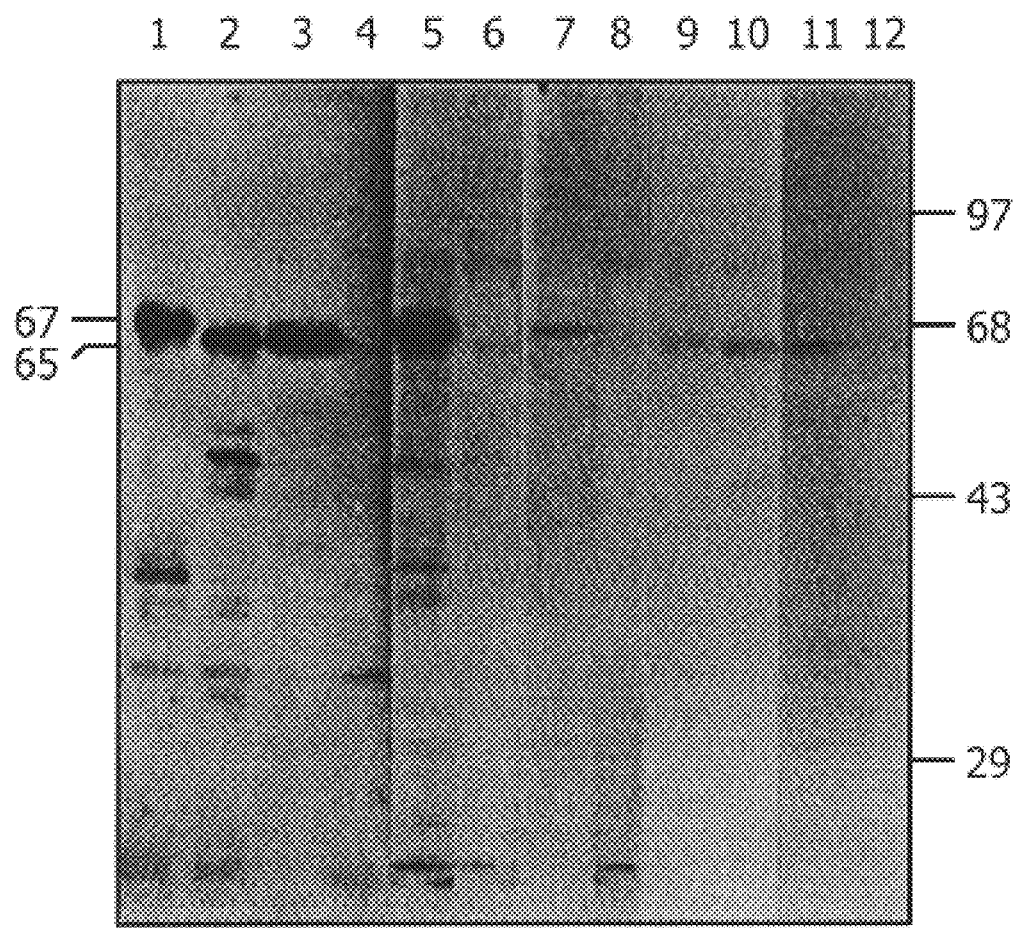
FIG. 7 Immunological identification of GAD$_{65}$ and GAD$_{67}$.

The immunoblots of bacterially produced $GAD_{65}$ and $GAD_{67}$ demonstrated that $GAD_{65}$ indeed corresponds to the smaller GAD in brain extracts, and $GAD_{67}$ to the larger form (FIG. 7). Previous work has demonstrated the correspondence of $GAD_{67}$ to the larger GAD for feline $GAD_{67}$, and for mouse $GAD_{67}$ (Katarova, et al., *Eur. J. Neurosci.*, 2:190, 1990; 235, 1987). The mobilities of bacterially produced $GAD_{65}$ and $GAD_{67}$ (as detected with the antiserum of Oertel, et al. (*Neuroscience*, 6:2689, 1981) are identical to the immunoreactive doublet seen in rat brain homogenate.

The smaller molecular weight and larger molecular weight forms of GAD in rat brain are thus identical in antigenicity and size to the products of $GAD_{65}$ and $GAD_{67}$ cDNAs, respectively. Consequently, the two GADs in rat brain are $GAD_{65}$ and $GAD_{67}$. From this data it can also be concluded that the molecular identity of the reported PLP-dependent and PLP-independent GADs by Tapia (Bayon, et al., *J. Neurochem.*, 29:519, 1977) are $GAD_{65}$ and $GAD_{67}$, respectively. Martin and coworkers (Spink, et al., Brain Res., 421:235, 1987) have reported the existence of four kinetically different forms of rat brain GAD. However, immunoblotting experiments (with the antisera used here) of these forms have not been reported.

E. DISTRIBUTION OF $GAD_{65}$ AND GAD $_7$ IN RNAs IN BRAIN TISSUE

Experiments were done to determine the distribution of $GAD_{65}$ and $GAD_{67}$ in RNAs in cerebellum using in situ hybridization.

Transcripts of, respectively, 3.2 kb and 2.3 kb from $GAD_{65}$ and $GAD_{67}$ cDNAs, were radiolabeled with $^{35}S$ according to Wuenschell, et al. (*Proc. Natl. Acad. Sci., USA*, 83:6193, 1986) procedure. Hydrolyzed fragments of 200 bp were hybridized to coronal sections of a rat cerebellum. Animals were anesthetized under halothane and decapitated. The brain was rapidly frozen in dry ice and coronal frozen sections (12 μm) were fixed for 30 min in freshly prepared 4% formaldehyde in phosphate-buffered saline (PBS; 130 mM NaCl, 10 mM Na phosphate, pH 7.0). The tissue was dehydrated through graded ethanol solutions and stored at −70° C.

In order to increase tissue permeability, the sections were submitted to the following pretreatments: rehydration through graded ethanol solutions (5 min each in 95%, 85%, 70%, 50%, and 30% ethanol); PBS (5 min); 0.02N HCl (10 min); PBS (5 min); 0.01% Triton N-101 in PBS (1 min); PBS (2×5 min); 1 μg/ml proteinase K (7.5 min); and glycine (to inhibit proteinase K) in PBS (3×5 min). Proteinase K was digested for 30 min at 37° C. before use. Sections were then incubated at 37° C. in 50% formamide, 750mM NaCl, 25 mM EDTA, 0.2% SDS, 0.02% BSA, 0.002% Ficoll, 0.02% polyvinylpyrrolidone, 250 μg/ml yeast tRNA, 250 μg/ml poly A, and 25 mM PPES (pH 6.8).

For the hybridization, 100 mM DTT, 10% dextran sulfate, and sense or antisense $^{35}$S-RNA were added to the prehybridization solution. An aliquot (50 μl) of the hybridization solution containing about 3 ng ($10^6$ cpm) of probe (sense or antisense) was added onto the slides. Each slide was coverslipped and incubated for 16 hrs at 50° C., following which the siliconized coverslips were removed by brief washing in 4×SSC (1×SSC—150 mM NaCl, 60 mM Na citrate, pH 7.0).

Sections were then treated with ribonuclease A (50 μg/ml in 0.5M NaCl, 10 mM Na thiosulfate, 1 mM EDTA, 10 mM TrisHCL, pH 8.0) for 20 min at 37° C. and rinsed for 2 hrs at room temperature in 2×SSC, 10 mM Na thiosulfate, for 30 min at 55° C. Sections were dehydrated in ethanol, delipidated in xylene, coated with Kodak NTB2 emulsion and exposed for 10 days at 4° C. The emulsion was developed with Kodak D19, and the tissue counterstained with cresyl violet.

Autoradiographic grains were detected using reflected polarized light and grain numbers, densities, nd cell areas were determined with an Analytic Imaging Concepts image analyzer system. Due to the low background level, the criteria for defining a cell "labeled" was based on the presence of more than 5 clustered grains. The GAD labeled cells were found scattered throughout the brain, enabling the measurement of the number of grains over individual cells. The boundary of the cell and the area covered by a grain allowed the calculation of the number of grains per cell. This analysis was done at a high magnification (800X), using both reflected polarized light and transmitted light to simultaneously visualize the stained cell and the superimposed grains. Numbers are means ±S.E.M. of "n" cells.

TABLE 2

| CELL TYPE | GRAINS/CELL | | |
|---|---|---|---|
| | $GAD_{67}$mRNA | $GAD_{65}$mRNA | $GAD_{67}$:$GAD_{65}$ |
| Purkinje | 172 ± 34 (87) | 43 2 (70) | 4.0 |
| Golgi II | 96 ± 8 (80) | 64 9 (65) | 1.5 |
| Basket | 61 ± 12 (102) | 16 1 (57) | 3.8 |
| Stellate | 55 ± 15 (65) | 18 3 (37) | 3.1 |

[a]S.E.M.(n)

In all neuronal types $GAD_{67}$ mRNA levels are greater. The observations with insitu hybridization are consistent with previous findings (Nitsch, J. Neurochem., 34:822, 1980; Denner, et al., J. Neurochem., 44:957, 1985; ltoh, et al., Neurochem. Res. 6:1283, 1981) that the ratio of PLP dependent to independent GAD activities in the cerebellum is one of the lowest in brain regions tested. In addition, as shown in Table 2, the order of amounts for $GAD_{67}$ mRNA is Purkinje>Golgi II>Basket>Stellate cells; in contrast, for $GAD_{67}$ mRNA, this order is Golgi II>Purkinje>Basket>Stellate cells.

The expression of $GAD_{65}$ and $GAD_{67}$ mRNAs thus differs among classes of neurons. The contribution of each to total GAD activity in turn affects how GABA production is regulated. For example, the substantia nigra contains one of the highest ratios of PLP-Dependent to PLP-independent GAD activities (Nitsch, J. Neurochem., 34:822, 1980). Increasing GABA concentration in the substantia nigra by local injection of inhibitors of GABA catabolism is especially effective in reducing seizure susceptibility (Gale, Fed. Proc., 44:2414, 1985). Experimental animals undergoing seizures indu ced by PLP-antagonists may t herefore be unable to inhibit seizure propagation because of inhibition of $GAD_{65}$ particularly in nerve terminals within the substantia nigra.

F. SUBCELLULAR LOCATION OF $GAD_{65}$ AND $GAD_{67}$

The distribution of $GAD_{65}$ and $GAD_{67}$ was evaluated in the $S_2$ and synaptosome subcellular fractions. $S_2$ is a high speed supernatant consisting of the cytosol of all cells in the brain, while the synaptosomal fraction consists primarily of nerve endings (Gray, et al., J. Anat., Lond, 96:79, 1962). For these studies, whole rat brain fractionation was performed as described by Booth and Clark (Booth, et al., Biochem. J., 176:365, 1978). Protein concentrations were determined by Schaffner and Weissman (Schaffner, et al., Anal. Biochem. 56:502, 1973). Samples were prepared as described (Kaiser, et al., DNA Cloning, Vol.I, A Practical Approach, D. M. Glover ed. (IRL Press, Oxford, 1985, pp. 38–40), and immunoblotting was done as described above using GAD-6 monoclonal antibody and K-2 antiserum. Equal amounts of protein (16 μg) were added to each lane. Autoradiography showed a linear response of increasing amount of $^{125}$I-protein A bound to antibody with protein concentrations of 1, 3, 10, 30, 100 μgs with both K-2 antiserum and GAD-6 monoclonal antibody (data not shown).

The results showed that $GAD_{67}$ was present in equal amounts in both fractions. Since the $S_2$ fraction contains the cytosolic proteins of glial (as well as other non-neuronal) and neuronal cells, the concentration of $GAD_{67}$ must be greater in neuronal cell bodies than in nerve endings. In contrast, the concentration of $GAD_{65}$ was greater in synaptosomes than in $S_2$. These subcellular fractionation experiments suggest that, in contrast to $GAD_{65}$, a much greater fraction of $GAD_{67}$ is present in cell bodies of neurons than in nerve terminals. Thus, subcellular fractionation, like immunohistochemistry, shows that $GAD_{65}$ and $GAD_{67}$ have different subcellular distributions.

In vivo experiments utilizing inhibitors of GABA synthesis and degradation have suggested that the GABA pool in neuronal cell bodies is different from that in the nerve terminals (ladarola, et al., Mol. Cell. Biochem., 39:305, 1981). GABA produced by $GAD_{67}$ may be involved more in cellular metabolism (for example, in the GABA shunt) and in dendrodendritic synapses. The dendrites of granule cells in the olfactory bulb, which form dendrodendritic synapses with mitral dendrites (Shepard, Physiol. Rev., 52:864, 1972) and probably release GABA (McLennan, Brain Res., 29:177–184, 1971), label intensely with K-2 antiserum. While not shown here, it has also been found greater $GAD_{67}$ than $GAD_{65}$ mRNA levels (2–3 fold) in the olfactory bulb. This distribution is consistent with the reported finding that most GAD activity in the olfactory bulb is present in $S_2$ and $P_1$ (crude nuclear pellet) and not in synaptosomes (Quinn, et al., *J. Neurochem.*, 35:583, 1980).

The differing subcellular distributions of $GAD_{65}$ and $GAD_{67}$ could result from cytoskeletal anchoring or from some unknown protein targeting mechanism. Some cytoskeletal proteins have distributions that resemble $GAD_{65}$ and $GAD_{65}$. For example, in cultured sympathetic neurons Peng, et al. (*J Cell. Biol.*, 102:252, 1986), demonstrate that 84% of tau is in axons while 100% of MAP-2 is in cell bodies and dendrites. In addition, 43 kd protein, a cytoskeletal protein, is thought to anchor the acetylcholine receptor to the underlying membrane cytoskeleton (Flucher, et al., *Neuron*, 3:163, 1989).

EXAMPLE 3

DETECTION OF GAD AUTOANTIBODIES IN CLINICAL SPECIMENS

A. MATERIALS AND METHODS

1. Patient Specimens. Sera from four groups of individuals were selected from a previous study by Atkinson and co-workers (Atkinson, et aL, Lancet, 335:1357–1360, 1990). These groups consisted of: Group (1), 1 new onset IDD patients diagnosed according to the established National Diabetes Data Group (NDDG) criteria (Gleichman, et al., *Diabetes*, 36:578–584, 1987) that had been referred to the University of Florida, Diabetes Clinics; Group (2), 5 randomly selected islet cell cytoplasmic antibody (ICA) negative non-diabetic controls without any known family history of autoimmune disease; Group (3), 13 individuals whose sera had been collected 3 to 66 months prior to their documented clinical onsets of IDD; Group (4), non-diabetic controls and relatives, and those who were studied prior to their onsets of IDD; and Group (5), 3 patients at risk for IDDM, but where onset has not yet occurred. This latter group had been ascertained through ongoing prospective ICA screening studies of more than 5000 first degree relative of IDD probands, and 8200 individuals from the general population (of which 4813 were school children).

2. Islet Cell Autoantibodies. ICA were assayed by indirect immunofluorescence on blood group O cryocut pancreatic (Atkinson, et al., *Lancet*, 335:1357–1360, 1990). All results were interpreted on coded samples, with control negative and positive sera in each batch. The degrees of ICA positivity were analyzed with the guidelines established by the Immunology Diabetes Workshop (IDW) for the standardization of ICA (Gleichman, et al., *Diabetes*, 36:578–584, 1987). All positive sera were titered by end point dilution, and the Juvenile Diabetes Foundation (JDF) units were determined by reference to a standard serum previously calibrated to the international JDF standard of 80 units. In the studies reported here, a positive ICA result was defined by replicate titers of 10 JDF units or greater.

3. HLA DR Typing. HLA DR typing was performed as adapted from the method described by Van Rood and Van Leuwen (*Nature*, 262:795–797, 1976), using DR trays (One Lamda Laboratories, Los Angeles, Calif.).

4. Human Islet Cells. Human pancreatic islets were isolated from cadaveric pancreases and maintained in vitro as previously described (Ricordi, et al., *Diabetes*, 37:413–420, 1988). The islet cells were metabolically labeled with $^{35}S$ methionine (Amersham, Arlington Heights, Ill.) in vitro (95% air/5% $CO_2$).

5. Islet Cell Extractions and Immunoprecipitations. Islet cells were extracted as previously described by Atkinson, et al. (*Lancet*, 335:1357–1360, 1990) with the following modifications. For immunoprecipitation studies, the islet cell lysates were precleared twice by incubation (2 h, 4° C.) with either control, IDD serum (100 µl), or GAD-6 (Chang, et al., *J. Neuro*, 8:2123–2130, 1988) (1 µl in 99 µl of Tris buffer (Atkinson, et al., *Lancet*, 335:1357–1360, 1990) for every 1000 islets. Immune complexes were then absorbed (1 h 4° C.) with an excess of protein A Sepharose CL-4B (Pharmacia, N.J.). Aliquot volumes representing 1000 islet cells containing unbound (precleared) lysate were then incubated (12 h, 4° C.) with either IDD or control sera (25 µl), or GAD-6 (Chang, et al., *J. Neuro*, 8:2123–2130, 1988) (1 µl in 25 µl Tris buffer). Following another incubation with protein A Sepharose CL-4B (1 h, 4° C.), the complexes were then washed 5 times with 50 mM Tris HCL (pH 7.4) with 0.1% SDS, 1.0% Triton X-114, and 2 mM EDTA, and then washed again one time in double distilled water. The protein A Sepharose CL-4B was then boiled in Laemmli sample buffer (Laemmli, *Nature*, 227:680–685, 1970), and the samples were subjected to SDS-PAGE and fluororadiography (Kodak, X-omat AR5) using Enhance (New England Nuclear). Alternatively, the autoradiographs were analyzed by a BETAGEN (Boston, Mass.) analyzer. Both 64 KA positive and negative sera were used in each assay, to serve as interassay controls. All fluororadiographs were analyzed and rated as positive or negative after comparison with the known interassay controls. Positive serum samples were designated as 1 when a sample resulted in immunoprecipitation of a low intensity 64,000 $M_x$ band, 2 if a moderate intensity band was observed and 3 if the intensity of the immunoprecipitated protein was high. A similar rating procedure was employed for the intensity of bands corresponding to immunoprecipitated $^{35}S$-$GAD_{65}$ and $^{35}S$-$GAD_{67}$.

6. Immunoprecipitations. Immunoprecipitation of bacterial lysates containing $^{35}S$-$GAD_{65}$ or $^{35}S$-$GAD_{67}$, and GAD from human brain homogenate, was completed as described above in immunoprecipitation studies of human islet cell extractions.

7. GAD Assays. Human brain homogenates were incubated with patient sera as described above in human islet cells. After absorption and washes, the protein A agarose slurry was aliquoted into three equal volumes and GAD activity was measured as described (Krieger, et al., *Neurochem.* 33:299, 1984). Briefly, Protein A agarose beads were incubated with (1-$^{14}C$)-glutamate (Amersham) in a designated incubation mixture (Krieger, et al., *Neurochem.* 33:299, 1984) and production of $^{14}CO_2$ was quantitated by a liquid scintillation counter.

8. Production of $^{35}S$-$GAD_{65}$ and $^{35}S$-$GAD_{67}$. Rat $GAD_{65}$ and $GAD_{67}$ cDNAs were subcloned into a bacterial expression system as previously described. Labeling of $^{35}S$-GADs was completed by pulsing IPTG induced bacterium (growing in Minimal Media) for 15 minutes with TRAN $^{35}S$-label (ICN). Cultures were then spun down and resuspended and sonicated in 1 ml of homogenizing buffer (1 mM phenylmethylsulfonyl fluoride (PMSF), 1 mM 2-aminoethylisothiouronium Bromide (AET) and 60 mM potassium phosphate, pH 7.1). After sonication, cell debris was removed by centrifugation and protein concentration was measured (Bradford, *Anal. Biochem.*, 72:248, 1986) in the supernatant (supernatant was stored in aliquots at −70° C.).

B. IMMUNOREACTIVITY OF IDDM SPECIMENS

Sera from patients with IDDM were tested for the ability to precipitate GAD from human brain homogenates.

TABLE 3

SERA FROM IDDM PATIENTS
IMMUNOPRECIPITATE GAD ACTIVITY

| Patient | IDDM | Pre-IDDM Period[1] | 64K[2] | JDF[3] | GAD Activity[4] cpm's |
|---|---|---|---|---|---|
| DA | *[5] | >24 | 3 | 164 | 13,762 |
| DC | * | >1 | 3 | 20 | 1,719 |
| RS | + | 5 | 3 | 40 | 588 |
| NL | + | 0 | 2 | 80 | 440 |
| DM | * | >1 | 2 | 10 | 184 |
| C | — | na | 0 | 0 | 280 |
| C | — | na | 0 | 0 | 285 |
| C | — | na | 0 | 0 | 325 |
| C | — | na | 0 | 0 | 275 |
| C | — | na | 0 | 0 | 270 |

[1]Expressed as months
[2]64K titers as described in Experimental Methods
[3]The islet cell antibody test as expressed in Juvenile Diabetes Foundation (JDF) units
[4]Not adjusted for background
[5]At risk for diabetes (also, failed glucose test)
na - Not applicable

TABLE 4

IDDM PATIENTS ANALYZED FOR AUTOANTIBODIES
PRIOR TO THE ONSET OF DISEASE

| Patient | Sex | HLA | Age Onset[1] | Pre-IDD Period[2] | JDF | 64 KA[3] | $GAD^3_{65}$ | $GAD^3_{67}$ |
|---|---|---|---|---|---|---|---|---|
| TA | M | 3,2 | 17 | 11 | 20 | 2 | 0 | 1 |
| CA | F | 4,5 | 38 | 4 | 0 | 1 | 1 | 0 |
| RA | M | 2,1 | 5 | 34 | 0 | 2 | 1 | 0 |
| TB | M | 2,4 | 11 | 66 | 40 | 1 | 1 | 0 |
| AB | M | N.D. | 23 | 6 | 160 | 3 | 3 | 2 |
| VC | F | 4,6 | 15 | 3 | 40 | 1 | 0 | 1 |
| JD | M | 6,1 | 34 | 25 | 10 | 3 | 1 | 1 |
| DR | F | 3,4 | 14 | 42 | 320 | 2 | 1 | 0 |
| JG | M | 3,3 | 12 | 8 | 40 | 1 | 0 | 0 |
| BR | M | 3,3 | 5 | 9 | 0 | 0 | 1 | 1 |
| KR | F | 4,X | 34 | 14 | 10 | 3 | 2 | 0 |
| JT | F | 4,6 | 7 | 10 | N.D. | 1 | 1 | 1 |

[1]Age of IDDM onset expressed as months
[2]The time interval between sera drawn and IDDM onset expressed as months
[3]1 = lowest; 2 = medium; and 3 = highest band intensities
N.D. - not determined As shown in Table 3, the sera of four (out of five) at risk for IDDM or IDDM patients bound significantly greater amounts of enzymatically active GAD of human brain extracts than sera from control patients. In addition, sera from one of the patients was drawn in a pre-IDDM period, thus autoantibodies to GAD are present prior to the onset of IDDM symptoms (see C below).

Further experiments (results not presented) showed that the sera of two at risk IDDM patients (DA, DC) immunoprecipitated recombinantly produced $^{35}$S-GAD$_{65}$ whereas recombinantly produced $^{35}$S-GAD$_{67}$ was only recognized by sera of patient DA (and to a lesser degree than $^{35}$S-GAD$_{65}$). Subsequent studies have found larger titers of GAD$_{67}$ autoantibodies than GAD$_{65}$ are present in sera of IDDM patients with neuropathic complications (not shown here).

Additional studies using patient DA sera showed the presence of antibodies which recognize specific polypeptides produced in human pancreatic islet cells. Electrophoretic analysis of the bound polypeptides demonstrated the presence of autoantibodies to a 64 kD component, as previously shown by others in human IDDM (Baekkeskov, et al., *Nature*, 298:167–169, 1982) and in animal models (Baekkeskov, et al., *Science*, 224:1348–1350, 1984; Atkinson, et al., *Diabetes*, 37:1587–1590, 1988). Prior absorption of these sera with GAD-6 monoclonal, which recognized GAD$_{65}$ but not GAD$_{67}$, or with bacterially produced GAD$_{65}$, abolished the ability of the sera to recognize the 64 kD pancreatic polypeptide. The epitopes recognized by autoantibodies to the 64 kD autoantigen are thus present in GAD$_{65}$, indicating that the autoantigen is indeed GAD$_{65}$. In order to investigate the predictive value of GAD$_{65}$, sera drawn from patients prior to onset of clinical manifestation of IDDM were tested for autoantibodies to GAD$_{65}$.

As shown in Table 4, 9 out of 12 specimens (75%) were immunoreactive with $^{35}$S-GAD$_{65}$. In addition, two patients (JA and VC) were immunoreactive to GAD$_{67}$, but not GAD$_{65}$ under these conditions. Therefore, in combination, autoantibodies to GAD$_{65}$ and GAD$_{67}$ were present in 11 out of 12 (91%) of these patients sera. This finding suggests that although autoantibodies to GAD$_{65}$ are more common than autoantibodies to GAD$_{67}$, the use of both recombinant GADs (GAD$_{65}$ and GAD$_{67}$) in an assay would allow for greater predictability of IDDM. Previous tests of these sera (Atkinson, et al., *Langet*, 335:1357–1360, 1990) demonstrated that 11 out of 12, or 92%, immunoreacted with the $^{35}$S-64 kD molecule from human pancreatic islet cells. The serum which contained detectable autoantibodies to the 64 kD molecule and not GAD$_{65}$ was a serum which contained the lowest titer (or "1") for the 64 kD molecule. Thus, the false negative obtained was due to a lack of sensitivity in this assay. Furthermore, this assay predicted IDDM in one patient (BR) who was negative for 64 K.

These results show that the 64 kD molecule identified in β-cells of human pancreas is identical in size and antigenicity to rat GAD$_{65}$. Furthermore, sera drawn from patients prior to IDDM onset contain autoantibodies to GAD$_{65}$. Consequently, the GAD$_{65}$ recombinant molecule is of great utility as a diagnostic tool for predicting IDDM. The ability of a physician to diagnose IDDM prior to actual symptoms will no doubt result in a greater extension of time before insulin therapy is needed. The sensitivity of such immunoassays will improve with the use of a recombinant GAD$_{65}$ of human origin which represents the GAD form present in β-cells of the pancreas.

The invention now being fully described, it will be apparent to one of ordinary skill in the art that many changes and modifications can be made without departing from the spirit or scope of the invention.

What is claimed is:

1. A method of detecting the presence of autoantibodies to glutamic acid decarboxylase (GAD) in a biological sample, the method comprising: contacting the sample with an isolated and purified recombinant GAD polypeptide produced by a cell transformed or transfected with a construct for expressing said GAD polypeptide, which construct comprises a DNA sequence encoding said GAD polypeptide wherein said sequence comprises the nucleotide sequence of FIG. 2 or FIG. 3, or a nucleotide sequence degenerate thereto which codes for the GAD polypeptide encoded by said nucleotide sequence of FIG. 2 or FIG. 3, wherein the polypeptide catalyzes the synthesis of γ-aminobutyric acid, and detecting the presence of immune complex formation between said GAD polypeptide and autoantibodies to GAD and therefrom detecting the presence of autoantibodies to GAD in the sample.

2. The method of claim 1, wherein the GAD polypeptide is attached to a solid support.

3. The method of claim 1, wherein the GAD polypeptide is labeled.

4. The method of claim 1, wherein said immune complex is detected by a second antibody.

5. The method of claim 1, wherein said detecting step is by enzyme reaction, colloidal metals, fluorescence, luminescence, or radioactivity.

6. The method of claim 1, wherein the sample is urine, saliva, cerebrospinal fluid, blood, serum tissue or feces.

* * * * *